United States Patent [19]
Hammond

[11] Patent Number: 5,906,917
[45] Date of Patent: May 25, 1999

[54] NUCLEIC ACID PROBES TO MYCOBACTERIUM TUBERCULOSIS

[75] Inventor: Philip W. Hammond, San Diego, Calif.

[73] Assignee: Gen-Probe Incorporated, San Diego, Calif.

[21] Appl. No.: 08/418,897

[22] Filed: Apr. 7, 1995

Related U.S. Application Data

[63] Continuation of application No. 07/876,283, Apr. 28, 1992, abandoned.
[51] Int. Cl.$^6$ .............................. C07H 21/04; C12Q 1/68; C12P 19/34
[52] U.S. Cl. ..................... 435/6; 435/91.2; 536/24.32; 536/24.33
[58] Field of Search ................... 435/6, 91.2; 536/24.32, 536/24.33; 935/77, 78, 8

[56] References Cited

U.S. PATENT DOCUMENTS

| | | | |
|---|---|---|---|
| 4,851,330 | 7/1989 | Kohne | 435/6 |
| 5,030,557 | 7/1991 | Hogan et al. | 435/6 |
| 5,168,039 | 12/1992 | Crawford et al. | 435/6 |
| 5,183,737 | 2/1993 | Crawford et al. | 435/6 |
| 5,216,143 | 6/1993 | Hogan et al. | 536/24.32 |
| 5,521,300 | 5/1996 | Shah et al. | 536/24.32 |

FOREIGN PATENT DOCUMENTS

| | | |
|---|---|---|
| 0229442 | 7/1987 | European Pat. Off. . |
| 0288618 | 11/1988 | European Pat. Off. . |
| 0318245 | 5/1989 | European Pat. Off. . |
| 0272009 | 11/1989 | European Pat. Off. . |
| 0398677 | 11/1990 | European Pat. Off. . |
| 0461045 | 6/1991 | European Pat. Off. . |
| 0461045 | 12/1991 | European Pat. Off. . |
| 8803957 | 6/1988 | WIPO . |
| 8803195 | 3/1989 | WIPO . |
| 8803361 | 4/1989 | WIPO . |

OTHER PUBLICATIONS

Rogall et al., "Towards a Phylogeny and Definition of Species at the Molecular Level within the Genus Mycobacterium," *International Journal of Systematic Bacteriology* 40:323–330 (1990).

Liesack, W. et al. Complete Nucleotide Sequence of the Mycobacterium LepRae 23S and 5SrRNA Genes Plus Flanking . . . FEBS Letters (1991) 281:114–118.

Gutell. et al. A Complication of Large Subunit RNA Sequences in a Structural Format. Nucl. Acids Res. (1988) vol. 16 (Supplement), pp. R–175–R269.

Regensburger, A, et al. Complete Nucleotide Sequence of a 23S Ribosom 1 RNA Gene From Micrococcuslutens. Nucl. Acids Res (1988) 16:2344.

GenAlign Computer Alignment of *M. leprae* and *M. luteus* 23S–Ribosomal RNAS.

Barone, A.D. et al., *Nucleic Acids Research*, "In situ activation of bis–dialkylaminophosphines—a new method for synthesizing deoxyoligonycleotides on polymer supports", 12:4051–4061, (1984).

Sambrook et al., *Molecular Cloning*, "Synthetic Oligonucleotide Probes", 2:11, (2d ed. 1989).

Arnold, L.J. et al., *Clinical Chemistry*, "Assay Formats Involving Acridinium–Ester–Labeled DNA Probes", 35:1588–1594., (1989).

Cox R.A. et al., *J. Med. Microbiol.*, "The 16S ribosomal RNA of *Mycobacterium leprae* contains a unique sequence which can be used for identification by the polymerase chain reaction", 35:284–290, (1991).

Tyagi, J.S. et al., *Trop. Med. Parasitol.*, "Transfer RNA genes in mycobacteria: organization and molecular cloning", 41:294–296, (1990).

Chemical Abstracts, vol. 93, Abstr. No. 144345, Liu et al., "Oligonucleotides for Typing of Mycobacteria," WO 9304201 A1, Mar. 4, 1993.

*Primary Examiner*—Carla J. Myers
*Attorney, Agent, or Firm*—Lyon & Lyon LLP

[57] ABSTRACT

Hybridization assay probes specific for members of the *Mycobacterium tuberculosis* Complex and no other Mycobacterium species.

47 Claims, No Drawings

NUCLEIC ACID PROBES TO MYCOBACTERIUM TUBERCULOSIS

This application is a continuation of application Ser. No. 07/876,283 now abadoned, filed Apr. 28, 1992.

FIELD OF THE INVENTION

The inventions described and claimed herein relate to the design and construction of nucleic acid probes for *Mycobacterium tuberculosis* Complex (TB Complex) which are capable of detecting the organisms in test samples for, e.g., sputum, urine, blood and tissue sections, food, soil and water.

BACKGROUND OF THE INVENTION

Two single strands of deoxyribo- ("DNA") or ribo- ("RNA") nucleic acid, formed from nucleotides (including the bases adenine (A), cytosine (C), thymidine (T), guanine (G), uracil (U), or inosine (I)), may associate ("hybridize") to form a double stranded structure in which the two strands are held together by hydrogen ponds between pairs of complementary bases. Generally, A is hydrogen bonded to T or U, while G is hydrogen bonded to C. At any point along the chain, therefore, one may find the classical base pairs AT or AU, TA or UA, GC, or CG. One may also find AG, GU and other "wobble" or mismatched base pairs.

When a first single strand of nucleic acid contains sufficient contiguous complementary bases to a second, and those two strands are brought together under conditions which will promote their hybridization, double stranded nucleic acid will result. Under appropriate conditions, DNA/DNA, RNA/DNA, or RNA/RNA hybrids may be formed.

A probe is generally a single stranded nucleic acid sequence which is complementary to some degree to a nucleic acid sequence sought to be detected ("target sequence"). It may be labelled with a detectable moiety such as a radioisotope, antigen or chemiluminescent moiety. A background description of the use of nucleic acid hybridization as a procedure for the detection of particular nucleic acid sequences is described by Kohne, U.S. Pat. No. 4,851,330, and Hogan et al., EPO Patent Application No. PCT/US87/03009, entitled "Nucleic Acid Probes for Detection and/Or Quantitation of Non-Viral Organisms."

Hogan et al., supra, also describes methods for determining the presence of RNA-containing organisms in a sample which might contain such organisms. These methods require probes sufficiently complementary to hybridize to the ribosomal RNA (rRNA) of one or more non-viral organisms or groups of non-viral organisms. The mixture is then incubated under specified hybridization conditions, and assayed for hybridization of the probe and any test sample rRNA.

Hogan et al. also describes probes which detect only specifically targeted rRNA subunit subsequences in particular organisms or groups of organisms in a sample, even in the presence of many non-related organisms, or in the presence of the closest known phylogenetic neighbors. Specific examples of hybridization assay probes are provided for *Mycobacterium tuberculosis*. Such probe sequences do not cross react with nucleic acids from other bacterial species or infectious agent, under appropriate hybridization stringency conditions.

SUMMARY OF THE INVENTION

This invention discloses and claims novel probes for the detection of *Mycobacterium tuberculosis* (TB) Complex. These probes are capable of distinguishing between the *Mycobacterium tuberculosis* Complex and its known closest phylogenetic neighbors. The *Mycobacterium tuberculosis* Complex consists of the following species: *M. tuberculosis, M. bovis, M. bovis* BCG, *M. africanum, M. microti*. These probes detect unique rRNA and gene sequences encoding rRNA, and may be used in an assay for the detection and/or quantitation of *Mycobacterium tuberculosis* Complex.

Organisms of the TB Complex are responsible for significant morbidity and mortality in humans. *M. tuberculosis* is the most common TB Complex pathogen isolated from humans. *M. bovis* BCG may be transmitted from infected animals to humans. *M. africanum* causes pulmonary tuberculosis in tropical Africa and *M. microti* primarily infects animals.

Tuberculosis is highly contagious, therefore rapid diagnosis of the disease is important. For most clinical laboratories assignment of an isolate to the TB Complex is sufficient because the probability that an isolate is a species other than *M. tuberculosis* is extremely small. A number of biochemical tests are recommended to speciate members of the TB Complex if further differentiation is required.

Classical methods for identification of mycobacteria rely on staining specimens for acid fast bacilli followed by culture and biochemical testing. It could take as long as two months to speciate an isolate using these standard methods. The use of DNA probes of this invention identifies TB Complex isolated from culture in less than an hour.

Thus, in a first aspect, the invention features a hybridization assay probe able to distinguish *Mycobacterium tuberculosis* from other Mycobacterium species; specifically, the probe is an oligonucleotide which hybridizes to the rRNA of the species *Mycobacterium tuberculosis* at a location corresponding to 23 bases in the insert region beginning at the equivalent of base 270 of *E. coli* 23S rRNA, or to 21 bases in the insert region beginning at the equivalent of base 1415 of *E. coli* 23S rRNA, or an oligonucleotide complementary thereto; that is, the oligonucleotide comprises, consists essentially of, or consists of the sequence (SEQ ID NO: 1) GGTAGCGCTGAGACATATCCTCC, or (SEQ ID NO: 2) CAGAACTCCACACCCCCGAAG, or oligonucleotides complementary thereto, with or without a helper probe, as described below.

By "consists essentially of" is meant that the probe is provided as a purified nucleic acid which hybridizes under stringent hybridizing conditions with the desired organism and not with other related organisms. Such a probe may be linked to other nucleic acids which do not affect such hybridization. Generally, it is preferred that the probe be of between 15 and 100 (most preferably between 20 and 50) bases in size. It may, however, be provided in a vector.

In related aspects, the invention features a nucleotide polymer able to hybridize to the above oligonucleotides, a nucleic acid hybrid formed with the above oligonucleotides, and a nucleic acid sequence substantially complementary thereto. Such hybrids are useful since they allow specific detection of the TB complex organisms.

The probes of this invention offer a rapid, non-subjective method of identification and quantitation of a bacterial colony for the presence of specific rRNA sequences unique to all species and strains of *Mycobacterium tuberculosis* Complex.

Other features and advantages of the invention will be apparent from the following description of the preferred embodiments thereof, and from the claims.

DESCRIPTION OF THE PREFERRED EMBODIMENTS

Probes

We have discovered DNA probes complementary to a particular rRNA sequence obtained from *Mycobacterium tuberculosis*. Furthermore, we have successfully used those probes in a specific assay for the detection of *Mycobacterium tuberculosis*, distinguishing members of the *M. tuberculosis* complex from their known and presumably most closely related taxonomic or phylogenetic neighbors.

We have identified suitable variable regions of the target nucleic acid by comparative analysis of rRNA sequences both published in the literature and sequences which we have determined. Computers and computer programs which may be used or adapted for the purposes herein disclosed are commercially available. Since the sequence evolution at each of the variable regions (for example, spanning a minimum of 10 nucleotides) is, for the most part, divergent, not convergent, we can confidently design probes based on a few rRNA sequences which differ between the target organism and its phylogenetically closest relatives. We have seen sufficient variation between the target organism and the closest phylogenetic relative found in the same sample to design the probe of interest.

We have identified the following useful guidelines for designing probes with desired characteristics. Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the probe:target nucleic acid hybrid should be chosen to be compatible with the assay conditions. This may be accomplished by avoiding long A and T rich sequences, by terminating the hybrids with G:C base pairs, and by designing the probe with an appropriate Tm. The beginning and end points of the probe should be chosen so that the length and %G and %C result in a Tm about 2–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as the ionic strength of the reaction mixture increases, and that the thermal stability of hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form (i.e., those having at least about 14 out of 17 bases in a contiguous series of bases being complementary); hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid.

Second, probes should be positioned so as to minimize the stability of the probe:nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible. Whether a probe sequence is useful to detect only a specific type of organism depends largely on the thermal stability difference between probe:target hybrids and probe:nontarget hybrids. In designing probes, the differences in these Tm values should be as large as possible (e.g., at least 2° C. and preferably 5° C.).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions of the rRNA which are known to form strong internal structures inhibitory to hybridization are less preferred. Likewise, probes with extensive self-domplementarity should be avoided.

As explained above, hybridization is the association of two single strands of complementary nucleic acid to form a hydrogen bonded double strand. It is implicit that if one of the two strands is wholly or partially involved in a hybrid that it will be less able to participate in formation of a new hybrid. In the case of rRNA, the molecule is known to form very stable intra-molecular hybrids. By designing a probe so that a substantial portion of the sequence of interest is single stranded, the rate and extent of hybridization may be greatly increased. If the target is the genomic sequence corresponding to the rRNA then it will naturally occur in a double stranded form, this is also the case with the product of the polymerase chain reaction (PCR). These double stranded targets are naturally inhibitory to hybridization with a probe. Finally, there can be intramolecular and intermolecular hybrids formed within a probe if there is sufficient self complementarity. Such structures can be avoided through careful probe design. Computer programs are available to search for this type of interaction.

Once a presumptive unique sequence has been identified, a complementary DNA oligonucleotide is produced. This single stranded oligonucleotide will serve as the probe in the hybridization reaction. Defined oligonucleotides may be produced by any of several well known methods, including automated solid-phase chemical synthesis using cyanoethylphosphoramidite precursors. Barone et al., 12 *Nucleic Acids Research* 4051, 1984. Other well-known methods for construction of synthetic oligonucleotides may, of course, be employed. Sambrook et al., 2 *Molecular Cloning* 11 (2d ed. 1989).

Once synthesized, selected oligonucleotide probes may also be labelled by any of several well known methods. Sambrook et al., supra. Useful labels include radio-isotopes as well as non-radioactive reporting groups. Isotopic labels include $^{3}H$, $^{35}S$, $^{32}P$, $^{125}I$, Cobalt and $^{14}C$. Most methods of isotopic labelling involve the use of enzymes and include the known methods of nick translation, end labelling, second strand synthesis, and reverse transcription. When using radio-labelled probes, hybridization can be detected by autoradiography, scintillation counting, or gamma counting. The detection method selected will depend upon the hybridization conditions and the particular radio-isotope used for labelling.

Non-isotopic materials can also be used for labelling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, chemiluminescent molecules, enzymes, cofactors, enzyme substrates, haptens or other ligands. We currently prefer to use acridinium esters.

Following synthesis and purification of a particular oligonucleotide sequence, several procedures may be utilized to determine the acceptability of the final product. The first is polyacrylamide gel electrophoresis, which is used to determine size. Sambrook et al., supra. Such procedures are known in the art. In addition to polyacrylamide gel electrophoresis, High Pressure Liquid Chromatography ("HPLC") procedures also may be used to determine the size and purity of the oligonucleotide product. These procedures are also known to those skilled in the art.

It will be appreciated by those skilled in the art that factors which affect the thermal stability can affect probe specificity and therefore, must be controlled. Thus, the melting profile, including the melting temperature (Tm) of the oligonucleotide/target hybrids should be determined. The preferred method is described in Arnold et al., PCT/US88/03195, filed Sep. 21, 1988, entitled "Homogeneous Protection Assay," hereby incorporated by reference herein.

For Tm measurement using a Hybridization Protection Assay (HPA) the following technique is used. A probe:target hybrid is formed in target excess in a lithium succinate buffered solution containing lithium lauryl sulfate. Aliquots of this hybrid are diluted in the hybridization buffer and incubated for five minutes at various temperatures starting below that of the anticipated Tm (typically 55° C.) and increasing in 2–5 degree increments. This solution is then diluted with a mildly alkaline borate buffer and incubated at a lower temperature (for example 50° C.) for ten minutes. Under these conditions the acridinium ester attached to a single stranded probe is hydrolyzed while that attached to hybridized probe is relatively protected from hydrolysis. The amount of chemiluminescence remaining is proportional to the amount of hybrid, and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In addition to the above method, oligonucleotide/target hybrid melting temperature may also be determined by isotopic methods well known to those skilled in the art. It should be noted that the Tm for a given hybrid will vary depending on the hybridization solution being used because the thermal stability depends upon the concentration of different salts, detergents, and other solutes which effect relative hybrid stability during thermal denaturation. Sambrook et al., supra.

Rate of hybridization may be measured by determining the $C_0t_{1/2}$. The rate at which a probe hybridizes to its target is a measure of the thermal stability of the target secondary structure in the probe region. The standard measurement of hybridization rate is the $C_0t_{1/2}$ which is measured as moles of nucleotide per liter times seconds. Thus, it is the concentration of probe times the half-life of hybridization at that concentration. This value is determined by hybridizing various amounts of probe to a constant amount of hybrid for a fixed time. For example, 0.05 pmol of target is incubated with 0.0012, 0.025, 0.05, 0.1 and 0.2 pmol of probe for 30 minutes. The amount of hybrid after 30 minutes is measured by HPA as described above. The signal is then plotted as a log of the percent of maximum Relative Light Units (RLU) (from the highest probe concentration) versus probe concentration (moles of nucleotide per liter). RLU are a measurement of the quantity of photons emitted by the labelled-probe measured by the luminometer. The $C_0t_{1/2}$ is found graphically from the concentration corresponding to 50% of maximum hybridization multiplied by the hybridization time in seconds. These values range from $9.0 \times 10^{-6}$ to $9 \times 10^{-5}$ with the preferred values being less than $3.5 \times 10^{-5}$.

As described by Kohne and Kacian (EP 86304429.3, filed Jun. 10, 1986), hereby incorporated by reference herein) other methods of nucleic acid reassociation can be used.

The following example sets forth synthetic probes complementary to a unique rRNA sequence, or the corresponding gene, from a target organism, *Mycobacterium tuberculosis*, and their use in a hybridization assay.

EXAMPLE

A probe specific for *M. tuberculosis* was identified by sequencing with a primer complementary to the 16S rRNA. The following sequences were characterized and shown to be specific for *Mycobacterium tuberculosis*; (SEQ ID NO: 1) GGTAGCGCTGAGACATATCCTCC, and (SEQ ID NO: 2) CAGAACTCCACACCCCCGAAG. Several phylogenetically near neighbors including *M. kansasii*, *M. asiaticum* and *M. avium* were used as comparisons with the sequence of *M. tuberculosis*. SEQ ID NO: 1 is 23 bases in length and hybridizes to the 23S rRNA of *M. tuberculosis* corresponding to bases 270–293 of *E. coli*. SEQ ID NO: 2 is 21 bases in length and hybridizes to the 23S rRNA of *M. tuberculosis* corresponding to bases 1415–1436 of *E. coli*.

To demonstrate the reactivity and specificity of the probe for *M. tuberculosis*, it was used in a hybridization assay. The probe was first synthesized with a non-nucleotide linker, then labelled with a chemiluminescent acridinium ester as described in EPO Patent Application No. PCT/US88/03361, entitled "Acridinium Ester Labeling and Purification of Nucleotide Probes filed Oct. 5, 1988. The acridinium ester attached to unhybridized probe is rendered non-chemiluminescent under mild alkaline conditions, while the acridinium ester attached to hybridized probe is relatively resistant. Thus, it is possible to assay for hybridization of acridinium ester-labelled probe by incubation with an alkaline buffer, followed by detection of chemiluminescence in a luminometer. Results are given in RLU, the quantity of photons emitted by the labelled-probe measured by the luminometer. The conditions of hybridization, hydrolysis and detection are described in Arnold, et al., 35 *Clin. Chem.* 1588, 1989.

Nucleic acid hybridization was enhanced by the use of "Helper Probes" as disclosed in Hogan et al., U.S. Pat. No. 5,030,557 hereby incorporated by reference herein. RNA was hybridized to the acridinium ester-labeled probe in the presence of an unlabeled Helper Probe. The probe corresponding to oligonucleotide SEQ ID NO: 1 with helpers:
(SEQ ID NO: 3) CCGCTAACCACGACACTTTCTG-TACTGCCTCTCAGCCG and
(SEQ ID NO: 4) CACAACCCCGCACACACAAC-CCCTACCCGGTTACCC.
The probe corresponding to oligonucleotide SEQ ID NO: 2 with helpers: (SEQ ID NO: 5) TGATTCGTCACGGGCGCCCACACACGGG-TACGGGAATATCAACCC and
(SEQ ID NO: 6) CTACTACCAGCCGAAGTTCCCACG-CAGCCC and (SEQ ID NO: 7) GGAGTTGATCGATCCG-
GTTTTGGGTGGTTAGTACCGC and
(SEQ ID NO: 8) GGGGTACGGGCCGTGTGTGT-
GCTCGCTAGAGGCTTTTCTTGGC.

In the following experiment, RNA released from one colony or >10$^8$ organisms was assayed. An example of such a method is provided by Murphy et al. (EP 873036412, filed Apr. 24, 1987), hereby incorporated by reference herein. An RLU value greater than 30,000 RLU is a positive reaction; less than 30,000 is a negative reaction.

The following data show that the probes did riot cross react with organisms from a wide phylogenetic cross section. The samples were also tested with a Probe (ALL BACT.) which has a very broad specificity to provide a positive control. A positive signal from this probe provides confirmation of sample adequacy.

| NAME | ATCC # | ALL BACT. | PROBE 1 | PROBE 2 |
|---|---|---|---|---|
| Mycobacterium africanum | 25420 | 880551 | 489764 | 589419 |
| M. asiaticum | 25276 | 1291076 | 708 | 1849 |
| M. avium | 25291 | 966107 | 615 | 1749 |
| M. bovis | 19210 | 1564761 | 1020088 | 717186 |
| M. bovis BCG | 35734 | 1532845 | 943131 | 706773 |
| M. chelonae | 14472 | 1581603 | 641 | 1320 |
| M. flavescens | 14474 | 237900 | 842 | 2001 |
| M. fortuitum | 6841 | 910478 | 641 | 1710 |
| M. gastri | 15754 | 429144 | 781 | 2416 |
| M. gordonae | 14470 | 1207443 | 749 | 2089 |
| M. haemophilum | 29548 | 709966 | 1090 | 3149 |
| M. intracellulare | 13950 | 277790 | 823 | 2512 |
| M. kansasii | 12478 | 416752 | 839 | 5688 |
| M. malmoense | 29571 | 149699 | 1176 | 4060 |
| M. marinum | 927 | 524740 | 699 | 3200 |
| M. nonchromogenicum | 19530 | 1541506 | 832 | 3303 |
| M. phlei | 11758 | 1273753 | 717 | 2286 |
| M. scrofulaceum | 19981 | 801447 | 1424 | 5236 |
| M. shimoidei | 27962 | 1609154 | 719 | 2650 |
| M. simiae | 25275 | 1571628 | 841 | 3152 |
| M. smegmatis | 14468 | 513995 | 789 | 2920 |
| M. szulgai | 35799 | 947710 | 714 | 2356 |
| M. terrae | 15755 | 480465 | 1492 | 7153 |
| M. thermoresistibile | 19527 | 1054152 | 1436 | 4113 |
| M. triviale | 23292 | 1016207 | 1148 | 4693 |
| M. tuberculosis (avir.) | 25177 | 1067974 | 767698 | 620393 |
| M. tuberculosis (vir.) | 27294 | 1543369 | 1012711 | 652815 |
| M. ulcerans | 19423 | 1401905 | 2563 | 5865 |
| M. vaccae | 15483 | 586428 | 729 | 3784 |
| M. xenopi | 19250 | 310648 | 855 | 3198 |
| Acinetobacter calcoaceticus | 33604 | 1393489 | 1735 | 9659 |
| Actinomadura madurae | 19425 | 572956 | 4388 | 5614 |
| Actinomyces pyogenes | 19411 | 1768540 | 1376 | 2527 |
| Arthrobacter oxydans | 14358 | 1542696 | 721 | 2126 |
| Bacilius subtilis | 6051 | 1441824 | 2424 | 2817 |
| Bacteriodes fragilis | 23745 | 1557888 | 843 | 8907 |
| Bordetella bronchiseptica | 10580 | 1694010 | 686 | 4113 |
| Branhamella catarrhalis | 25238 | 1615709 | 1035 | 7219 |
| Brevibacterium linens | 9172 | 904166 | 814 | 1642 |
| Campylobacter jejuni | 33560 | 1824094 | 607 | 3201 |
| Candida albicans | 18804 | 3850 | 763 | 2018 |
| Chromobacterium violaceum | 29094 | 1560283 | 993 | 11823 |
| Clostridium innocuum | 14501 | 1571465 | 577 | 2072 |
| C. perfringens | 13124 | 1701191 | 641 | 5757 |
| Corynebacterium aquaticum | 14665 | 1616486 | 801 | 1865 |
| C. diphtheriae | 11913 | 1464829 | 682 | 1475 |
| C. genitalium | 33030 | 108105 | 1177 | 1797 |
| C. haemolyticum | 9345 | 1512544 | 703 | 1114 |
| C. matruchotii | 33806 | 1871454 | 659 | 1967 |
| C. minutissimum | 23347 | 1024206 | 586 | 1302 |
| C. pseudodiphtheriticum | 10700 | 1605944 | 578 | 1155 |
| C. pseudogenitalium | 33035 | 497387 | 717 | 1324 |
| C. pseudotuberculosis | 19410 | 1730057 | 643 | 2892 |
| C. renale | 19412 | 1467841 | 544 | 1743 |
| C. striatum | 6940 | 1560152 | 602 | 1386 |
| C. xerosis | 373 | 1211115 | 651 | 1556 |
| Deinococcus radiodurans | 35073 | 1387623 | 644 | 1400 |
| Dermatophilus congolensis | 14637 | 1551500 | 810 | 2075 |
| Derxia gumosa | 15994 | 1735694 | 4676 | 4797 |
| Erysipelothrix rhusiopathiae | 19414 | 1623646 | 564 | 1180 |
| Escherichia coli | 10798 | 1685941 | 581 | 4610 |
| Flavobacterium meniningosepticum | 13253 | 1571895 | 1037 | 4626 |
| Haemophilus influenzae | 19418 | 1706963 | 668 | 2303 |
| Klebsiella pneumoniae | 23357 | 1692364 | 639 | 6673 |
| Lactobacillus acidophilus | 4356 | 226596 | 780 | 1619 |
| Legionella pneuinophila | 33152 | 1666343 | 755 | 4184 |
| Microbacterium lacticum | 8180 | 620978 | 514 | 924 |
| Mycoplasma hominis | 14027 | 1305131 | 496 | 1410 |
| M. pneumoniae | 15531 | 1605424 | 481 | 1428 |
| Neisseria meningitidis | 13077 | 1684295 | 1531 | 8802 |
| Nocardia asteriodes | 19247 | 1265198 | 1037 | 1938 |
| N. brasiliensis | 19296 | 1483481 | 759 | 1737 |
| N. otitidis-caviarum | 14629 | 1462489 | 813 | 1791 |
| Nocardiopsis dassonvillei | 23218 | 662986 | 4052 | 4960 |
| Oerskovia turbata | 33225 | 1753101 | 591 | 1979 |
| O. xanthineolytica | 27402 | 1712806 | 721 | 1639 |
| Paracoccus denitrificans | 17741 | 958719 | 771 | 2910 |
| Proteus mirabilis | 25933 | 1761750 | 669 | 2545 |
| Pseudomonas aeruginosa | 25330 | 1730788 | 1281 | 6048 |
| Rahnella aquatilis | 33071 | 1728428 | 485 | 2884 |
| Rhodococcus aichiensis | 33611 | 528199 | 595 | 1169 |
| R. aurantiacus | 25936 | 1737076 | 616 | 2310 |
| R. bronchialis | 25592 | 1695267 | 635 | 1633 |
| R. chubuensis | 33609 | 1079495 | 599 | 1262 |
| R. equi | 6939 | 1762242 | 709 | 2863 |
| R. obuensis | 33610 | 658848 | 686 | 1482 |
| R. sputi | 29627 | 814617 | 719 | 1419 |
| Staphylococcus aureus | 12598 | 1687401 | 636 | 1434 |
| S. epidermidis | 12228 | 1117790 | 651 | 1255 |
| S. mitis | 9811 | 1807598 | 542 | 1199 |
| S. pneumoniae | 6306 | 1883301 | 532 | 1441 |
| S. pyogenes | 19615 | 1862392 | 728 | 1656 |
| Streptomyces griseus | 23345 | 1417914 | 1737 | 3378 |
| Vibrio parahaemolyticus | 17802 | 1767149 | 752 | 6429 |
| Yersinia enterocolitica | 9610 | 1769411 | 662 | 4255 |

The above data confirm that the novel probes herein disclosed and claimed are capable of distinguishing members of the *Mycobacterium tuberculosis* complex from their known nearest phylogenetic neighbors.

Other embodiments are within the following claims.

What is claim is:

1. A hybridization assay probe for detecting the presence of *Mycobacterium tuberculosis, Mycobacterium bovis, Mycobacterium bovis* BCG and *Mycobacterium africanum* nucleic acid, comprising an oligonucleotide which is 15 to 100 nucleotides in length containing at least 14 out of 17 contiguous bases perfectly complementary to a nucleic acid sequence selected from the group consisting of:
SEQ ID NO 1: GGTAGCGCTGAGACATATCCTCC,
SEQ ID NO 2: CAGAACTCCACACCCCCGAAG,
SEQ ID NO 10: GGUAGCGCUGAGACAUAUCCUCC,
SEQ ID NO 11: GGAGGAUAUGUCUCAGCGCUACC,
SEQ ID NO 13: CAGAACUCCACACCCCCGAAG, and
SEQ ID NO 14: CUUCGGGGGUGUGGAGUUCUG;
wherein said oligonucleotide hybridizes to *Mycobacterium tuberculosis, Mycobacterium bovis, Mycobacterium bovis* BCG and *Mycobacterium africanum* nucleic acid under high stringency hybridization conditions, wherein under said conditions said probe can distinguish *Mycobacterium tuberculosis, Mycobacterium bovis, Mycobacterium bovis* BCG and *Mycobacterium africanum* nucleic acid, from *Mycobacterium avium, Mycobacterium asiaticum*, and *Mycobacterium kansasii* nucleic acid.

2. The probe of claim 1, wherein said nucleic acid sequence is selected from the group consisting of: SEQ ID NO 2: CAGAACTCCACACCCCCGAAG, SEQ ID NO 13: CAGAACUCCACACCCCCGAAG, and SEQ ID NO 14: CUUCGGGGGUGUGGAGUUCUG.

3. The probe of claim 2, wherein said oligonucleotide comprises a nucleotide sequence selected from the group consisting of:
SEQ ID NO 2: CAGAACTCCACACCCCCGAAG,
SEQ ID NO 12: CTTCGGGGGTGTGGAGTTCTG,
SEQ ID NO 13: CAGAACUCCACACCCCCGAAG, and
SEQ ID NO 14: CUUCGGGGGUGUGGAGUUCUG.

4. The probe of claim 3, wherein said oligonucleotide is 21 to 50 bases in length.

5. The probe of claim 3, wherein said probe consists of said nucleotide sequence and one or more optionally present detectable labels, wherein said optionally present detectable labels may or may not be present.

6. The probe of claim 5, wherein said probe contains a detectable label selected from the group consisting of: radioisotope, fluorescent molecule, chemiluminescent molecule, enzyme, cofactor, enzyme substrate, and hapten.

7. The probe of claim 6, wherein said detectable label is an acridinium ester.

8. The probe of claim 1, wherein said nucleic acid sequence is selected from the group consisting of:
SEQ ID NO 1: GGTAGCGCTGAGACATATCCTCC,
SEQ ID NO 10: GGUAGCGCUGAGACAUAUCCUCC, and
SEQ ID NO 11: GGAGGAUAUGUCUCAGCGCUACC.

9. The probe of claim 8, wherein said oligonucleotide comprises a nucleotide sequence selected from the group consisting of:
SEQ ID NO 1: GGTAGCGCTGAGACATATCCTCC,
SEQ ID NO 9: GGAGGATATGTCTCAGCGCTACC,
SEQ ID NO 10: GGUAGCGCUGAGACAUAUCCUCC, and
SEQ ID NO 11: GGAGGAUAUGUCUCAGCGCUACC.

10. The probe of claim 9, wherein said oligonucleotide is 23 to 50 bases in length.

11. The probe of claim 9, wherein said probe consists of said nucleotide sequence and one or more optionally present detectable labels, wherein said optionally present detectable labels may or may not be present.

12. The probe of claim 11, wherein said probe contains a detectable label selected from the group consisting of: radioisotope, fluorescent molecule, chemiluminescent molecule, enzyme, cofactor, enzyme substrate, and hapten.

13. The probe of claim 12, wherein said detectable label is an acridinium ester.

14. A nucleic acid hybrid comprising:
a) a hybridization assay probe for detecting the presence of *Mycobacterium tuberculosis, Mycobacterium bovis, Mycobacterium bovis* BCG and *Mycobacterium africanum* nucleic acid, comprising an oligonucleotide which is 15 to 100 nucleotides in length containing at least 14 out of 17 contiguous bases perfectly complementary to a target nucleic acid sequence selected from the group consisting of:
SEQ ID NO 1: GGTAGCGCTGAGACATATCCTCC,
SEQ ID NO 2: CAGAACTCCACACCCCCGAAG,
SEQ ID NO 10: GGUAGCGCUGAGACAUAUCCUCC,
SEQ ID NO 11: GGAGGAUAUGUCUCAGCGCUACC, SEQ ID NO 13: CAGAACUCCACACCCCCGAAG, and
SEQ ID NO 14: CUUCGGGGGUGUGGAGUUCUG;
  wherein said oligonucleotide hybridizes to *Mycobacterium tuberculosis, Mycobacterium bovis, Mycobacterium bovis* BCG and *Mycobacterium africanum* nucleic acid under high stringency hybridization conditions, wherein under said conditions said probe can distinguish *Mycobacterium tuberculosis, Mycobacterium bovis, Mycobacterium bovis* BCG and *Mycobacterium africanum* nucleic acid, from *Mycobacterium avium, Mycobacterium asiaticum,* and *Mycobacterium kansasii* nucleic acid; and b) *Mycobacterium tuberculosis, Mycobacterium bovis, Mycobacterium bovis* BCG or *Mycobacterium africanum* nucleic acid containing a complementary region, said complementary region selected from the group consisting of:
  23S rRNA corresponding to bases 270–293 of *E. coli,*
  rDNA gene for 23S rRNA corresponding to bases 270–293 of *E. coli,*
  23S rRNA corresponding to bases 1415–1436 of *E. coli,* and
  rDNA gene for 23S rRNA corresponding to bases 1415–1436 of *E. coli.*

15. The hybrid of claim 14, wherein said target nucleic acid sequence is selected from the group consisting of:

SEQ ID NO 2: CAGAACTCCACACCCCCGAAG,

SEQ ID NO 13: CAGAACUCCACACCCCCGAAG, and

SEQ ID NO 14: CUUCGGGGGUGUGGAGUUCUG.

16. The hybrid of claim 15, wherein said oligonucleotide is 21 to 50 bases in length and comprises a nucleotide sequence selected from the group consisting of:

SEQ ID NO 2: CAGAACTCCACACCCCCGAAG,

SEQ ID NO 12: CTTCGGGGGTGTGGAGTTCTG,

SEQ ID NO 13: CAGAACUCCACACCCCCGAAG, and

SEQ ID NO 14: CUUCGGGGGUGUGGAGUUCUG.

17. The probe of claim 16, wherein said probe consists of said nucleotide sequence and one or more optionally present detectable labels, wherein said optionally present detectable labels may or may not be present.

18. The hybrid of claim 14, wherein said target nucleic acid sequence is selected from the group consisting of:

SEQ ID NO 1: GGTAGCGCTGAGACATATCCTCC,

SEQ ID NO 10: GGUAGCGCUGAGACAUAUCCUCC, and

SEQ ID NO 11: GGAGGAUAUGUCUCAGCGCUACC.

19. The hybrid of claim 18, wherein said oligonucleotide is 23 to 50 bases in length and comprises a nucleotide sequence selected from the group consisting of:

SEQ ID NO 1: GGTAGCGCTGAGACATATCCTCC,

SEQ ID NO 9: GGAGGATATGTCTCAGCGCTACC,

SEQ ID NO 10: GGUAGCGCUGAGACAUAUCCUCC, and

SEQ ID NO 11: GGAGGAUAUGUCUCAGCGCUACC.

20. The hybrid of claim 19, wherein said probe consists of said nucleotide sequence and one or more optionally present detectable labels, wherein said optionally present detectable labels may or may not be present.

21. A method for determining if at least one of *Mycobacterium tuberculosis, Mycobacterium bovis, Mycobacterium bovis* BCG and *Mycobacterium africanum* may be present in a sample comprising the steps of:

a) contacting said sample under high stringency hybridization conditions with a hybridization assay probe for detecting the presence of *Mycobacterium tuberculosis, Mycobacterium bovis, Mycobacterium bovis* BCG and *Mycobacterium africanum* nucleic acid, said probe comprising an oligonucleotide containing at least 14 out of 17 contiguous bases perfectly complementary to a nucleic acid sequence selected from the group consisting of:

SEQ ID NO 1: GGTAGCGCTGAGACATATCCTCC,

SEQ ID NO 2: CAGAACTCCACACCCCCGAAG,

SEQ ID NO 10: GGUAGCGCUGAGACAUAUCCUCC,

SEQ ID NO 11: GGAGGAUAUGUCUCAGCGCUACC,

SEQ ID NO 13: CAGAACUCCACACCCCCGAAG, and

SEQ ID NO 14: CUUCGGGGGUGUGGAGUUCUG;

wherein said oligonucleotide hybridizes to *Mycobacterium tuberculosis, Mycobacterium bovis, Mycobacterium bovis* BCG and *Mycobacterium africanum* nucleic acid under high stringency hybridization conditions, wherein under said conditions said probe can distinguish *Mycobacterium tuberculosis, Mycobacterium bovis, Mycobacterium bovis* BCG and *Mycobacterium africanum* nucleic acid, from *Mycobacterium avium, Mycobacterium asiaticum*, and *Mycobacterium kansasii* nucleic acid; and b) detecting hybridization of said probe to nucleic acid present in said sample under said high stringency hybridization conditions as an indication that at least one of *Mycobacterium tuberculosis, Mycobacterium bovis, Mycobacterium bovis* BCG and *Mycobacterium africanum* may be present.

22. The method of claim 21, wherein said nucleic acid sequence is selected from the group consisting of:

SEQ ID NO 2: CAGAACTCCACACCCCCGAAG,

SEQ ID NO 13: CAGAACUCCACACCCCCGAAG, and

SEQ ID NO 14: CUUCGGGGGUGUGGAGUUCUG.

23. The method of claim 22, wherein said oligonucleotide comprises a nucleotide sequence selected from the group consisting of:

SEQ ID NO 2: CAGAACTCCACACCCCCGAAG,

SEQ ID NO 12: CTTCGGGGGTGTGGAGTTCTG,

SEQ ID NO 13: CAGAACUCCACACCCCCGAAG, and

SEQ ID NO 14: CUUCGGGGGUGUGGAGUUCUG.

24. The method of claim 23, wherein said oligonucleotide is 21 to 50 bases in length.

25. The method of claim 23, wherein said probe consists of said nucleotide sequence and one or more optionally present detectable labels, wherein said optionally present detectable labels may or may not be present.

26. The method of claim 21, wherein said nucleic acid sequence is selected from the group consisting of:

SEQ ID NO 1: GGTAGCGCTGAGACATATCCTCC,

SEQ ID NO 10: GGUAGCGCUGAGACAUAUCCUCC, and

SEQ ID NO 11: GGAGGAUAUGUCUCAGCGCUACC.

27. The method of claim 26, wherein said oligonucleotide comprises a nucleotide sequence selected from the group consisting of:

SEQ ID NO 1: GGTAGCGCTGAGACATATCCTCC,

SEQ ID NO 9: GGAGGATATGTCTCAGCGCTACC,

SEQ ID NO 10: GGUAGCGCUGAGACAUAUCCUCC, and

SEQ ID NO 11: GGAGGAUAUGUCUCAGCGCUACC.

28. The method of claim 27, wherein said oligonucleotide is 23 to 50 bases in length.

29. The method of claim 27, wherein said probe consists of said nucleotide sequence and one or more optionally present detectable labels, wherein said optionally present detectable labels mav or may not be present.

30. A composition comprising:
   a) a hybridization assay probe for detecting the presence of *Mycobacterium tuberculosis, Mycobacterium bovis, Mycobacterium bovis* BCG and *Mycobacterium africanum* nucleic acid, said probe comprising an oligonucleotide which is 15 to 100 nucleotides in length containing at least 14 out of 17 contiguous bases perfectly complementary to a hybridization assay probe target nucleic acid sequence selected from the group consisting of:
   SEQ ID NO 1: GGTAGCGCTGAGACATATCCTCC,
   SEQ ID NO 2: CAGAACTCCACACCCCCGAAG,
   SEQ ID NO 10: GGUAGCGCUGAGACAUAUCCUCC,
   SEQ ID NO 11: GGAGGAUAUGUCUCAGCGCUACC,
   SEQ ID NO 13: CAGAACUCCACACCCCGAAG, and
   SEQ ID NO 14: CUUCGGGGUGUGGAGUUCUG;
   wherein said oligonucleotide hybridizes to *Mycobacterium tuberculosis, Mycobacterium bovis, Mycobacterium bovis* BCG and *Mycobacterium africanum* nucleic acid under said high stringency hybridization conditions, wherein under said conditions said probe can distinguish *Mycobacterium tuberculosis, Mycobacterium bovis, Mycobacterium bovis* BCG and *Mycobacterium africanum* nucleic acid, from *Mycobacterium avium, Mycobacterium asiaticum*, and *Mycobacterium kansasii* nucleic acid; and at least one helper probe comprising a helper probe nucleotide sequence selected from the group consisting of:
   SEQ ID NO: 3 CCGCTAACCA CGACACTTTC TGTACTGCCT CTCAGCCG,
   SEQ ID NO: 4 CACAACCCCG CACACACAAC CCCTACCCGG TTACCC,
   SEQ ID NO: 5 TGATTCGTCA CGGGCGCCCA CACACGGGTA CGGGAATATC AACCC,
   SEQ ID NO: 6 CTACTACCAG CCGAAGTTCC CACGCAGCCC,
   SEQ ID NO: 7 GGAGTTGATC GATCCGGTTT TGGGTGGTTA GTACCGC,
   SEQ ID NO: 8 GGGGTACGGG CCGTGTGTGT GCTCGCTAGA GGCTTTTCTT GGC,
   SEQ ID NO: 15 CGGCTGAGAG GCAGTACAGA AAGTGTCGTG GTTAGCGG,
   SEQ ID NO: 16 GGGTAACCGG GTAGGGGTTG TGTGTGCGGG GTTGTG,
   SEQ ID NO: 17 CCGCUAACCA CGACACUUUC UGUACUGCCU CUCAGCCG,
   SEQ ID NO: 18 CACAACCCCG CACACACAAC CCCUACCCGG UUACCC,
   SEQ ID NO: 19 CGGCUGAGAG GCAGUACAGA AAGUGUCGUG GUUAGCGG,
   SEQ ID NO: 20 GGGUAACCGG GUAGGGGUUG UGUGUGCGGG GUUGUG,
   SEQ ID NO: 21 GGGTTGATAT TCCCGTACCC GTGTGTGGGC GCCCGTGACG AATCA,
   SEQ ID NO: 22 GGGCTGCGTG GGAACTTCGG CTGGTAGTAG,
   SEQ ID NO: 23 GCGGTACTAA CCACCCAAAA CCGGATCGAT CAACTCC,
   SEQ ID NO: 24 GCCAAGAAAA GCCTCTAGCG AGCACACACA CGGCCCGTAC CCC,
   SEQ ID NO: 25 UGAUUCGUCA CGGGCGCCCA CACACGGGUA CGGGAAUAUC AACCC,
   SEQ ID NO: 26 CUACUACCAG CCGAAGUUCC CACGCAGCCC,
   SEQ ID NO: 27 GGAGUUGAUC GAUCCGGUUU UGGGUGGUUA GUACCGC,
   SEQ ID NO: 28 GGGGUACGGG CCGUGUGUGU GCUCGCUAGA GGCUUUUCUU GGC,
   SEQ ID NO: 29 GGGUUGAUAU UCCCGUACCC GUGUGUGGGC GCCCGUGACG AAUCA,
   SEQ ID NO: 30 GGGCUGCGUG GGAACUUCGG CUGGUAGUAG,
   SEQ ID NO: 31 GCGGUACUAA CCACCCAAAA CCGGAUCGAU CAACUCC, and
   SEQ ID NO: 32 GCCAAGAAAA GCCUCUAGCG AGCACACACA CGGCCCGUAC CCC.

31. The composition of claim 30, wherein said hybridization assay probe target nucleic acid sequence is selected from the group consisting of:
   SEQ ID NO 1: GGTAGCGCTGAGACATATCCTCC,
   SEQ ID NO 10: GGUAGCGCUGAGACAUAUCCUCC, and
   SEQ ID NO 11: GGAGGAUAUGUCUCAGCGCUACC;
   and said at least one helper probe comprises a helper probe nucleotide sequence selected from the group consisting of:
   SEQ ID NO: 3 CCGCTAACCA CGACACTTTC TGTACTGCCT CTCAGCCG,
   SEQ ID NO: 4 CACAACCCCG CACACACAAC CCCTACCCGG TTACCC,
   SEQ ID NO: 15 CGGCTGAGAG GCAGTACAGA AAGTGTCGTG GTTAGCGG,
   SEQ ID NO: 16 GGGTAACCGG GTAGGGGTTG TGTGTGCGGG GTTGTG,
   SEQ ID NO: 17 CCGCUAACCA CGACACUUUC UGUACUGCCU CUCAGCCG, and
   SEQ ID NO: 18 CACAACCCCG CACACACAAC CCCUACCCGG UUACCC.

32. The composition of claim 31, wherein said hybridization assay probe is 23 to 50 bases in length and comprises a hybridization assay probe nucleotide sequence selected from the group consisting of:
   SEQ ID NO 1: GGTAGCGCTGAGACATATCCTCC,
   SEQ ID NO 9: GGAGGATATGTCTCAGCGCTACC,
   SEQ ID NO 10: GGUAGCGCUGAGACAUAUCCUCC, and
   SEQ ID NO 11: GGAGGAUAUGUCUCAGCGCUACC.

33. The composition of claim 32, wherein said hybridization assay probe consists of said hybridization assay probe nucleotide sequence which is labeled, and said at least one helper probe consists of said helper probe nucleotide sequence.

34. The composition of claim 33, wherein said hybridization assay probe nucleotide sequence is either SEQ ID NO 1: GGTAGCGCTGAGACATATCCTCC or SEQ ID NO 10: GGUAGCGCUGAGACAUAUCCUCC; and said at least one helper probe consists of a first helper probe of SEQ ID NO: 3 CCGCTAACCA CGACACTTTC TGTACTGCCT CTCAGCCG, and a second helper probe of SEQ ID NO: 4 CACAACCCCG CACACACAAC CCCTACCCGG TTACCC.

35. The composition of claim 33, wherein said hybridization assay probe nucleotide sequence is either SEQ ID NO 9: GGAGGATATGTCTCAGCGCTACC, or SEQ ID NO 11: GGAGGAUAUGUCUCAGCGCUACC; and said at least one helper probe consists of a first helper probe of SEQ ID NO: 15 CGGCTGAGAG GCAGTACAGA AAGTGTCGTG GTTAGCGG, and a second helper probe of SEQ ID NO: 16 GGGTAACCGG GTAGGGGTTG TGTGTGCGGG GTTGTG.

36. The composition of claim 30, wherein said hybridization assay probe target nucleic acid sequence is selected from the group consisting of:

SEQ ID NO 2: CAGAACTCCACACCCCCGAAG,

SEQ ID NO 13: CAGAACUCCACACCCCCGAAG, and

SEQ ID NO 14: CUUCGGGGUGUGGAGUUCUG; and said at least one helper probe comprises a helper probe nucleotide sequence selected from the group consisting of:

SEQ ID NO: 5 TGATTCGTCA CGGGCGCCCA CACACGGGTA CGGGAATATC AACCC,

SEQ ID NO: 6 CTACTACCAG CCGAAGTTCC CACGCAGCCC,

SEQ ID NO: 7 GGAGTTGATC GATCCGGTTT TGGGTGGTTA GTACCGC,

SEQ ID NO: 8 GGGGTACGGG CCGTGTGTGT GCTCGCTAGA GGCTTTTCTT GGC,

SEQ ID NO: 25 UGAUUCGUCA CGGGCGCCCA CACACGGGUA CGGGAAUAUC AACCC,

SEQ ID NO: 26 CUACUACCAG CCGAAGUUCC CACGCAGCCC,

SEQ ID NO: 27 GGAGUUGAUC GAUCCGGUUU UGGGUGGUUA GUACCGC, and

SEQ ID NO: 28 GGGGUACGGG CCGUGUGUGU GCUCGCUAGA GGCUUUUCUU GGC.

37. The composition of claim 36, wherein said hybridization assay probe is 23 to 50 bases in length and comprises a hybridization assay probe nucleotide sequence selected from the group consisting of:

SEQ ID NO 2: CAGAACTCCACACCCCCGAAG,

SEQ ID NO 12: CTTCGGGGGTGTGGAGTTCTG,

SEQ ID NO 13: CAGAACUCCACACCCCCGAAG, and

SEQ ID NO 14: CUUCGGGGUGUGGAGUUCUG.

38. The composition of claim 37, wherein said hybridization assay probe consists of said hybridization assay probe nucleotide sequence which is labeled and said at least one helper probe consists of said helper probe nucleotide sequence.

39. The composition of claim 38, wherein said hybridization assay probe nucleotide sequence is either SEQ ID NO 2: CAGAACTCCACACCCCCGAAG, or SEQ ID NO 13: CAGAACUCCACACCCCCGAAG; and said at least one helper probe consists of a first helper probe of SEQ ID NO: 5 TGATTCGTCA CGGGCGCCCA CACACGGGTA CGGGAATATC AACCC, a second helper probe of SEQ ID NO: 6 CTACTACCAG CCGAAGTTCC CACGCAGCCC, a third helper probe of SEQ ID NO: 7 GGAGTTGATC GATCCGGTTT TGGGTGGTTA GTACCGC, and a fourth helper probe of SEQ ID NO: 8 GGGGTACGGG CCGTGTGTGT GCTCGCTAGA GGCTTTTCTT GGC.

40. A method for determining if at least one of *Mycobacterium tuberculosis, Mycobacterium bovis, Mycobacterium bovis* BCG and *Mycobacterium africanum* may be present in a sample comprising the steps of:

a) providing to said sample a nucleic acid hybridization assay probe which under hybridization buffer conditions employed during hybridization assay conditions hybridizes to *Mycobacterium tuberculosis, Mycobacterium bovis, Mycobacterium bovis* BCG and *Mycobacterium africanum* nucleic acid in a region corresponding to nucleotide position 270–292 of *E. coli* 16S rRNA or 1415–1435 of *E. coli* 23S rRNA, or the complements thereof, to form a probe:target hybrid with a Tm which is at least 2° C. greater than a probe:non-target hybrid formed with said region present in nucleic acid of *Mycobacterium avium, Mycobacterium asiaticum*, and *Mycobacterium kansasii*, and b) detecting whether probe:target hybrids have formed under said hybridization assay conditions as an indication that at least one of *Mycobacterium tuberculosis, Mycobacterium bovis, Mycobacterium bovis* BCG and *Mycobacterium africanum* may be present, wherein under said hybridization assay conditions detectable probe:non-target hybrids do not form.

41. The method of claim 40, wherein said region corresponds to nucleotide position 270–292 of *E. coli* 16S rRNA, or the complement thereof.

42. The method of claim 41, wherein under said hybridization buffer conditions employed during hybridization assay conditions said probe forms a probe:target hybrid with a Tm which is at least 5° C. greater than a probe:non-target hybrid formed with said region present in nucleic acid of *Mycobacterium avium, Mycobacterium asiaticum*, and *Mycobacterium kansasii*.

43. The method of claim 40, wherein said region corresponds to nucleotide position 1415–1435 of *E. coli* 23S rRNA, or the complement thereof.

44. The method of claim 43, wherein under said hybridization buffer conditions employed during hybridization assay conditions said probe forms a probe:target hybrid with a Tm which is at least 5° C. greater than a probe:non-target hybrid formed with said region present in nucleic acid of *Mycobacterium avium, Mycobacterium asiaticum*, and *Mycobacterium kansasii*.

45. A method for determining if at least one of *Mycobacterium tuberculosis, Mycobacterium bovis, Mycobacterium bovis* BCG and *Mycobacterium africanum* may be present in a sample comprising the steps of: a) exposing said sample to a hybridization assay means which detects whether a *Mycobacterium tuberculosis, Mycobacterium bovis, Mycobacterium bovis* BCG and *Mycobacterium africanum* nucleic acid target region located in a position corresponding to nucleotide position 270–292 of *E. coli* 16S rRNA or 1415–1435 of *E. coli* 23S rRNA, or the complements thereof, is present in said sample, and b) determining whether said means detects the presence of said target region in said sample as an indication that at least one of *Mycobacterium tuberculosis, Mycobacterium bovis, Mycobacterium bovis* BCG and *Mycobacterium africanum* may be present in said sample, provided that said means distinguishes *Mycobacterium tuberculosis, Mycobacterium bovis, Mycobacterium bovis* BCG and *Mycobacterium africanum* nucleic acid, from *Mycobacterium avium, Mycobacterium asiaticum*, and *Mycobacterium kansasii* nucleic acid.

46. The method of claim 45, wherein said target region corresponds to nucleotide position 270–292 of *E. coli* 16S rRNA, or the complement thereof.

47. The method of claim 45, wherein said target region corresponds to nucleotide position 1415–1435 of *E. coli* 23S rRNA, or the complement thereof.

\* \* \* \* \*

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 23
      (B) TYPE: nucleic acid
      (C) STRANDEDNESS: single
      (D) TOPOLOGY: linear (ii) SEQUENCE DESCRIPTION: SEQ ID NO: 1:

GGTAGCGCTG AGACATATCC TCC                              23

(2) INFORMATION FOR SEQ ID NO: 2:

(i) SEQUENCE CHARACTERISTICS:
      (A) LENGTH: 21
      (B) TYPE: nucleic acid
      (C) STRANDEDNESS: single
      (D) TOPOLOGY: linear (ii) SEQUENCE DESCRIPTION: SEQ ID NO: 2:

CAGAACTCCA CACCCCCGAA G                                21

(2) INFORMATION FOR SEQ ID NO: 3:

(i) SEQUENCE CHARACTERISTICS:
      (A) LENGTH: 38
      (B) TYPE: nucleic acid
      (C) STRANDEDNESS: single
      (D) TOPOLOGY: linear (ii) SEQUENCE DESCRIPTION: SEQ ID NO: 3:

CCGCTAACCA CGACACTTTC TGTACTGCCT CTCAGCCG               38

(2) INFORMATION FOR SEQ ID NO: 4:

(i) SEQUENCE CHARACTERISTICS:
      (A) LENGTH: 36
      (B) TYPE: nucleic acid
      (C) STRANDEDNESS: single
      (D) TOPOLOGY: linear (ii) SEQUENCE DESCRIPTION: SEQ ID NO: 4:

CACAACCCCG CACACACAAC CCCTACCCGG TTACCC                 36

(2) INFORMATION FOR SEQ ID NO: 5:

(i) SEQUENCE CHARACTERISTICS:
      (A) LENGTH: 45
      (B) TYPE: nucleic acid
      (C) STRANDEDNESS: single
      (D) TOPOLOGY: linear (ii) SEQUENCE DESCRIPTION: SEQ ID NO: 5:

TGATTCGTCA CGGGCGCCCA CACACGGGTA CGGGAATATC AACCC        45

(2) INFORMATION FOR SEQ ID NO: 6:

(i) SEQUENCE CHARACTERISTICS:
      (A) LENGTH: 30
      (B) TYPE: nucleic acid
      (C) STRANDEDNESS: single
      (D) TOPOLOGY: linear (ii) SEQUENCE DESCRIPTION: SEQ ID NO: 6:

CTACTACCAG CCGAAGTTCC CACGCAGCCC  30

(2) INFORMATION FOR SEQ ID NO: 7:

(i) SEQUENCE CHARACTERISTICS:
        (A) LENGTH: 37
        (B) TYPE: nucleic acid
        (C) STRANDEDNESS: single
        (D) TOPOLOGY: linear (ii) SEQUENCE DESCRIPTION: SEQ ID NO: 7:

GGAGTTGATC GATCCGGTTT TGGGTGGTTA GTACCGC  37

(2) INFORMATION FOR SEQ ID NO: 8:

(i) SEQUENCE CHARACTERISTICS:
        (A) LENGTH: 43
        (B) TYPE: nucleic acid
        (C) STRANDEDNESS: single
        (D) TOPOLOGY: linear (ii) SEQUENCE DESCRIPTION: SEQ ID NO: 8:

GGGGTACGGG CCGTGTGTGT GCTCGCTAGA GGCTTTTCTT GGC  43

(2) INFORMATION FOR SEQ ID NO: 9:

(i) SEQUENCE CHARACTERISTICS:
        (A) LENGTH: 23
        (B) TYPE: nucleic acid
        (C) STRANDEDNESS: single
        (D) TOPOLOGY: linear (ii) SEQUENCE DESCRIPTION: SEQ ID NO: 9:

GGAGGATATG TCTCAGCGCT ACC  23

(2) INFORMATION FOR SEQ ID NO: 10:

(i) SEQUENCE CHARACTERISTICS:
        (A) LENGTH: 23
        (B) TYPE: nucleic acid
        (C) STRANDEDNESS: single
        (D) TOPOLOGY: linear (ii) SEQUENCE DESCRIPTION: SEQ ID NO: 10:

GGUAGCGCUG AGACAUAUCC UCC  23

(2) INFORMATION FOR SEQ ID NO: 11:

(i) SEQUENCE CHARACTERISTICS:
        (A) LENGTH: 23
        (B) TYPE: nucleic acid
        (C) STRANDEDNESS: single
        (D) TOPOLOGY: linear (ii) SEQUENCE DESCRIPTION: SEQ ID NO: 11:

GGAGGAUAUG UCUCAGCGCU ACC  23

(2) INFORMATION FOR SEQ ID NO: 12:

(i) SEQUENCE CHARACTERISTICS:
        (A) LENGTH: 21
        (B) TYPE: nucleic acid
        (C) STRANDEDNESS: single
        (D) TOPOLOGY: linear (ii) SEQUENCE DESCRIPTION: SEQ ID NO: 12:

```
CTTCGGGGGT GTGGAGTTCT G                                                            21

(2) INFORMATION FOR SEQ ID NO:    13:

(i) SEQUENCE CHARACTERISTICS:
           (A) LENGTH:                  21
           (B) TYPE:                    nucleic acid
           (C) STRANDEDNESS:            single
           (D) TOPOLOGY:                linear (ii) SEQUENCE DESCRIPTION: SEQ ID NO: 13:

CAGAACUCCA CACCCCCGAA G                                                            21

(2) INFORMATION FOR SEQ ID NO:    14:

(i) SEQUENCE CHARACTERISTICS:
           (A) LENGTH:                  21
           (B) TYPE:                    nucleic acid
           (C) STRANDEDNESS:            single
           (D) TOPOLOGY:                linear (ii) SEQUENCE DESCRIPTION: SEQ ID NO: 14:

CUUCGGGGGU GUGGAGUUCU G                                                            21

(2) INFORMATION FOR SEQ ID NO:    15:

(i) SEQUENCE CHARACTERISTICS:
           (A) LENGTH:                  38
           (B) TYPE:                    nucleic acid
           (C) STRANDEDNESS:            single
           (D) TOPOLOGY:                linear (ii) SEQUENCE DESCRIPTION: SEQ ID NO: 15:

CGGCTGAGAG GCAGTACAGA AAGTGTCGTG GTTAGCGG                                          38

(2) INFORMATION FOR SEQ ID NO:    16:

(i) SEQUENCE CHARACTERISTICS:
           (A) LENGTH:                  36
           (B) TYPE:                    nucleic acid
           (C) STRANDEDNESS:            single
           (D) TOPOLOGY:                linear (ii) SEQUENCE DESCRIPTION: SEQ ID NO: 16:

GGGTAACCGG GTAGGGGTTG TGTGTGCGGG GTTGTG                                            36

(2) INFORMATION FOR SEQ ID NO:    17:

(i) SEQUENCE CHARACTERISTICS:
           (A) LENGTH:                  38
           (B) TYPE:                    nucleic acid
           (C) STRANDEDNESS:            single
           (D) TOPOLOGY:                linear (ii) SEQUENCE DESCRIPTION: SEQ ID NO: 17:

CCGCUAACCA CGACACUUUC UGUACUGCCU CUCAGCCG                                          38

(2) INFORMATION FOR SEQ ID NO:    18:

(i) SEQUENCE CHARACTERISTICS:
           (A) LENGTH:                  36
           (B) TYPE:                    nucleic acid
           (C) STRANDEDNESS:            single
           (D) TOPOLOGY:                linear (ii) SEQUENCE DESCRIPTION: SEQ ID NO: 18:

CACAACCCCG CACACACAAC CCCUACCCGG UUACCC                                            36
```

(2) INFORMATION FOR SEQ ID NO: 19:

(i) SEQUENCE CHARACTERISTICS:
        (A) LENGTH: 38
        (B) TYPE: nucleic acid
        (C) STRANDEDNESS: single
        (D) TOPOLOGY: linear (ii) SEQUENCE DESCRIPTION: SEQ ID NO: 19:

CGGCUGAGAG GCAGUACAGA AAGUGUCGUG GUUAGCGG                    38

(2) INFORMATION FOR SEQ ID NO: 20:

(i) SEQUENCE CHARACTERISTICS:
        (A) LENGTH: 36
        (B) TYPE: nucleic acid
        (C) STRANDEDNESS: single
        (D) TOPOLOGY: linear (ii) SEQUENCE DESCRIPTION: SEQ ID NO: 20:

GGGUAACCGG GUAGGGGUUG UGUGUGCGGG GUUGUG                      36

(2) INFORMATION FOR SEQ ID NO: 21:

(i) SEQUENCE CHARACTERISTICS:
        (A) LENGTH: 45
        (B) TYPE: nucleic acid
        (C) STRANDEDNESS: single
        (D) TOPOLOGY: linear (ii) SEQUENCE DESCRIPTION: SEQ ID NO: 21:

GGGTTGATAT TCCCGTACCC GTGTGTGGGC GCCCGTGACG AATCA           45

(2) INFORMATION FOR SEQ ID NO: 22:

(i) SEQUENCE CHARACTERISTICS:
        (A) LENGTH: 30
        (B) TYPE: nucleic acid
        (C) STRANDEDNESS: single
        (D) TOPOLOGY: linear (ii) SEQUENCE DESCRIPTION: SEQ ID NO: 22:

GGGCTGCGTG GGAACTTCGG CTGGTAGTAG                            30

(2) INFORMATION FOR SEQ ID NO: 23:

(i) SEQUENCE CHARACTERISTICS:
        (A) LENGTH: 37
        (B) TYPE: nucleic acid
        (C) STRANDEDNESS: single
        (D) TOPOLOGY: linear (ii) SEQUENCE DESCRIPTION: SEQ ID NO: 23:

GCGGTACTAA CCACCCAAAA CCGGATCGAT CAACTCC                   37

(2) INFORMATION FOR SEQ ID NO: 24:

(i) SEQUENCE CHARACTERISTICS:
        (A) LENGTH: 43
        (B) TYPE: nucleic acid
        (C) STRANDEDNESS: single
        (D) TOPOLOGY: linear (ii) SEQUENCE DESCRIPTION: SEQ ID NO: 24:

GCCAAGAAAA GCCTCTAGCG AGCACACACA CGGCCCGTAC CCC             43

(2) INFORMATION FOR SEQ ID NO:   25:

(i) SEQUENCE CHARACTERISTICS:
        (A) LENGTH:              45
        (B) TYPE:                nucleic acid
        (C) STRANDEDNESS:        single
        (D) TOPOLOGY:            linear (ii) SEQUENCE DESCRIPTION: SEQ ID NO: 25:

UGAUUCGUCA CGGGCGCCCA CACACGGGUA CGGGAAUAUC AACCC                45

(2) INFORMATION FOR SEQ ID NO:   26:

(i) SEQUENCE CHARACTERISTICS:
        (A) LENGTH:              30
        (B) TYPE:                nucleic acid
        (C) STRANDEDNESS:        single
        (D) TOPOLOGY:            linear (ii) SEQUENCE DESCRIPTION: SEQ ID NO: 26:

CUACUACCAG CCGAAGUUCC CACGCAGCCC                                 30

(2) INFORMATION FOR SEQ ID NO:   27:

(i) SEQUENCE CHARACTERISTICS:
        (A) LENGTH:              37
        (B) TYPE:                nucleic acid
        (C) STRANDEDNESS:        single
        (D) TOPOLOGY:            linear (ii) SEQUENCE DESCRIPTION: SEQ ID NO: 27:

GGAGUUGAUC GAUCCGGUUU UGGGUGGUUA GUACCGC                         37

(2) INFORMATION FOR SEQ ID NO:   28:

(i) SEQUENCE CHARACTERISTICS:
        (A) LENGTH:              43
        (B) TYPE:                nucleic acid
        (C) STRANDEDNESS:        single
        (D) TOPOLOGY:            linear (ii) SEQUENCE DESCRIPTION: SEQ ID NO: 28:

GGGGUACGGG CCGUGUGUGU GCUCGCUAGA GGCUUUUCUU GGC                  43

(2) INFORMATION FOR SEQ ID NO:   29:

(i) SEQUENCE CHARACTERISTICS:
        (A) LENGTH:              45
        (B) TYPE:                nucleic acid
        (C) STRANDEDNESS:        single
        (D) TOPOLOGY:            linear (ii) SEQUENCE DESCRIPTION: SEQ ID NO: 29:

GGGUUGAUAU UCCCGUACCC GUGUGUGGGC GCCCGUGACG AAUCA                45

(2) INFORMATION FOR SEQ ID NO:   30:

(i) SEQUENCE CHARACTERISTICS:
        (A) LENGTH:              30
        (B) TYPE:                nucleic acid
        (C) STRANDEDNESS:        single
        (D) TOPOLOGY:            linear (ii) SEQUENCE DESCRIPTION: SEQ ID NO: 30:

GGGCUGCGUG GGAACUUCGG CUGGUAGUAG                                 30

(2) INFORMATION FOR SEQ ID NO:   31:

```
    (i) SEQUENCE CHARACTERISTICS:
        (A) LENGTH:          37
        (B) TYPE:            nucleic acid
        (C) STRANDEDNESS:    single
        (D) TOPOLOGY:        linear (ii) SEQUENCE DESCRIPTION: SEQ ID NO: 31:

GCGGUACUAA CCACCCAAAA CCGGAUCGAU CAACUCC                                37

(2) INFORMATION FOR SEQ ID NO:     32:

(i) SEQUENCE CHARACTERISTICS:
        (A) LENGTH:          43
        (B) TYPE:            nucleic acid
        (C) STRANDEDNESS:    single
        (D) TOPOLOGY:        linear (ii) SEQUENCE DESCRIPTION: SEQ ID NO: 32:

GCCAAGAAAA GCCUCUAGCG AGCACACACA CGGCCCGUAC CCC                         43
```